US010052354B2

(12) United States Patent
Tobita et al.

(10) Patent No.: US 10,052,354 B2
(45) Date of Patent: Aug. 21, 2018

(54) ANTI-ALLERGIC COMPOSITION

(75) Inventors: Keisuke Tobita, Tokyo (JP); Hajime Otani, Nagano (JP)

(73) Assignee: KITII CO., LTD., Tokyo (JP)

( * ) Notice: Subject to any disclaimer, the term of this patent is extended or adjusted under 35 U.S.C. 154(b) by 124 days.

(21) Appl. No.: 13/583,266

(22) PCT Filed: Mar. 4, 2011

(86) PCT No.: PCT/JP2011/001291
§ 371 (c)(1),
(2), (4) Date: Sep. 7, 2012

(87) PCT Pub. No.: WO2011/114645
PCT Pub. Date: Sep. 22, 2011

(65) Prior Publication Data
US 2013/0045291 A1    Feb. 21, 2013

(30) Foreign Application Priority Data

Mar. 19, 2010 (JP) ................................ 2010-064451

(51) Int. Cl.
| | |
|---|---|
| *A61K 35/747* | (2015.01) |
| *A61K 35/744* | (2015.01) |
| *A23L 2/38* | (2006.01) |
| *C10M 111/04* | (2006.01) |
| *C10M 169/04* | (2006.01) |
| *A23K 10/18* | (2016.01) |
| *A23L 29/00* | (2016.01) |
| *A23L 33/135* | (2016.01) |
| *A61K 35/74* | (2015.01) |

(52) U.S. Cl.
CPC ............ *A61K 35/747* (2013.01); *A23K 10/18* (2016.05); *A23L 2/382* (2013.01); *A23L 29/065* (2016.08); *A23L 33/135* (2016.08); *A61K 35/74* (2013.01); *A61K 35/744* (2013.01); *C10M 111/04* (2013.01); *C10M 169/04* (2013.01); *C10M 2203/1006* (2013.01); *C10M 2205/0285* (2013.01); *C10M 2207/281* (2013.01); *C10M 2209/084* (2013.01); *C10M 2215/28* (2013.01); *C10M 2219/046* (2013.01); *C10M 2219/08* (2013.01); *C10M 2223/04* (2013.01); *C10M 2223/047* (2013.01); *C10M 2229/025* (2013.01); *C10M 2229/0415* (2013.01); *C10N 2220/021* (2013.01); *C10N 2220/022* (2013.01); *C10N 2230/02* (2013.01); *C10N 2230/68* (2013.01); *C10N 2240/04* (2013.01)

(58) Field of Classification Search
None
See application file for complete search history.

(56) References Cited

U.S. PATENT DOCUMENTS

| | | | | |
|---|---|---|---|---|
| 6,994,848 | B2 * | 2/2006 | Hsu .......................... | C12N 1/20 424/93.45 |
| 7,303,745 | B2 * | 12/2007 | Herz .................... | A61K 35/745 424/93.45 |
| 2004/0071679 | A1 * | 4/2004 | De Simone ............... | 424/93.45 |
| 2004/0110270 | A1 * | 6/2004 | Dennin ................ | A61K 35/742 435/252.5 |

FOREIGN PATENT DOCUMENTS

| | | | |
|---|---|---|---|
| EP | 0353581 | A2 | 7/1989 |
| EP | 1634600 | * | 3/2006 |
| EP | 1941892 | A2 | 12/2007 |
| JP | 09002959 | | 1/1997 |
| JP | 10309178 | | 11/1998 |
| JP | 2000095697 | | 4/2000 |
| JP | 2005068092 | | 3/2005 |
| JP | 2005137357 | | 6/2005 |
| JP | 2006067881 | | 3/2006 |
| JP | 2006104107 | | 4/2006 |
| JP | 2007055986 | | 3/2007 |
| JP | 2007070249 | | 3/2007 |
| JP | 2007117031 | | 5/2007 |
| JP | 2007126365 | | 5/2007 |
| JP | 2008054556 | | 3/2008 |
| JP | 2008061512 | | 3/2008 |
| JP | 2008099632 | | 5/2008 |
| JP | 2008169198 | | 7/2008 |
| JP | 2008231094 | | 10/2008 |
| JP | 2008255084 | | 10/2008 |

(Continued)

OTHER PUBLICATIONS

Machine translation of JP 2009-209132 Sep. 17, 2009.*
Ewaschuk et al. Can J Vet Res. Oct. 2004; 68(4):249-253).*
Google patent English translation of Morimoto et al JP2006067881A retrieved on Aug. 16, 2007 at: https://patents.google.com/patent/JP2006067881A/en.*
International Preliminary Report on Patentability, PCT/JP2011/001291, dated Nov. 1, 2012.
Database WPI Week 200875 Thomson Scientific, London, GB; AN 2008-M71613 XP002707995, & JP 2008 255084 A (Hashimoto I) Oct. 23, 2008 (Oct. 23, 2008) * abstract *.
Database WPI Week 200736 Thomson Scientific, London, GB; AN 2007-383259 XP002707996, & JP 2007 126365 A (Momoya KK) May 24, 2007 (May 24, 2007) * abstract *.

(Continued)

*Primary Examiner* — Oluwatosin A Ogunbiyi
(74) *Attorney, Agent, or Firm* — Edwin S. Flores; Daniel J. Chalker; Chalker Flores, LLP

(57) ABSTRACT

It is to provide a composition derived from lactic acid bacteria having an anti-allergic effect (an effect of suppressing allergic symptoms such as hay fever) synergistically, and a food product, pet food, etc. containing the composition. It is to prepare a composition having an anti-allergic action, containing *Lactobacillus crispatus* KT-11 strain, KT-23 strain, or KT-25 strain bacterial cells and viable bacteria, dead bacteria, or a processed product of bacterial cells of other lactic acid bacteria belonging to the genus *Lactobacillus*, genus *Bifidobacterium*, genus *Leuconostoc*, genus *Enterococcus*, genus *Pediococcus*, etc. at a biomass-converted ratio of 99:1 to 50:50, preferably 99:1 to 75:25.

1 Claim, 2 Drawing Sheets

(56) References Cited

FOREIGN PATENT DOCUMENTS

| | | |
|---|---|---|
| JP | 2009057346 | 3/2009 |
| JP | 2009112232 | 5/2009 |
| JP | 2009142266 | 7/2009 |
| JP | 2009209132 | 9/2009 |
| JP | 2009242275 | 10/2009 |
| WO | 00/78322 A2 | 12/2000 |
| WO | 2000078322 A2 | 12/2000 |

OTHER PUBLICATIONS

Extended European Search Report (EP 11755838.7) dated Aug. 7, 2013.
Tobita, Keisure, et al., "Heat-Treated Lactobacillus crispatus KT Strains Reduce Allergic Symptoms in Mice," J. Agric. Food Chem., 2009, 57, 5586-5590.

* cited by examiner

[Fig. 1]
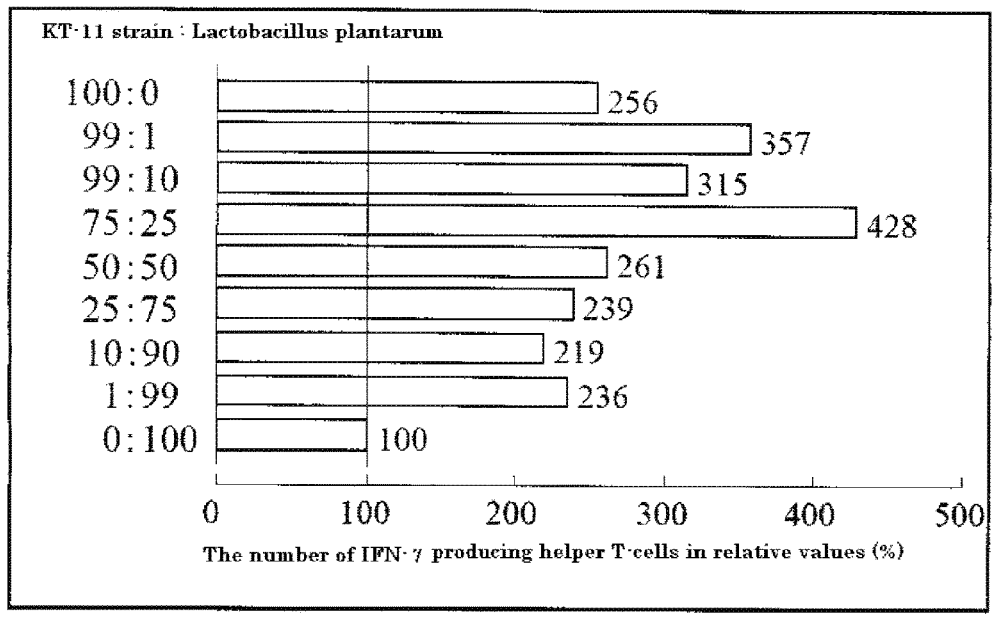
[Fig. 2]
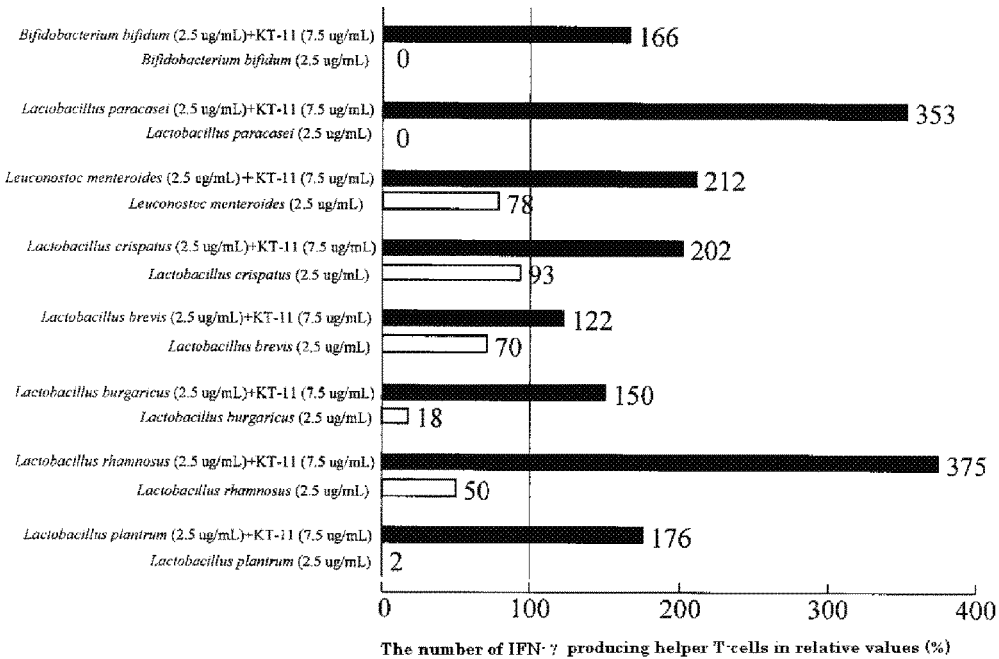

[Fig. 3]
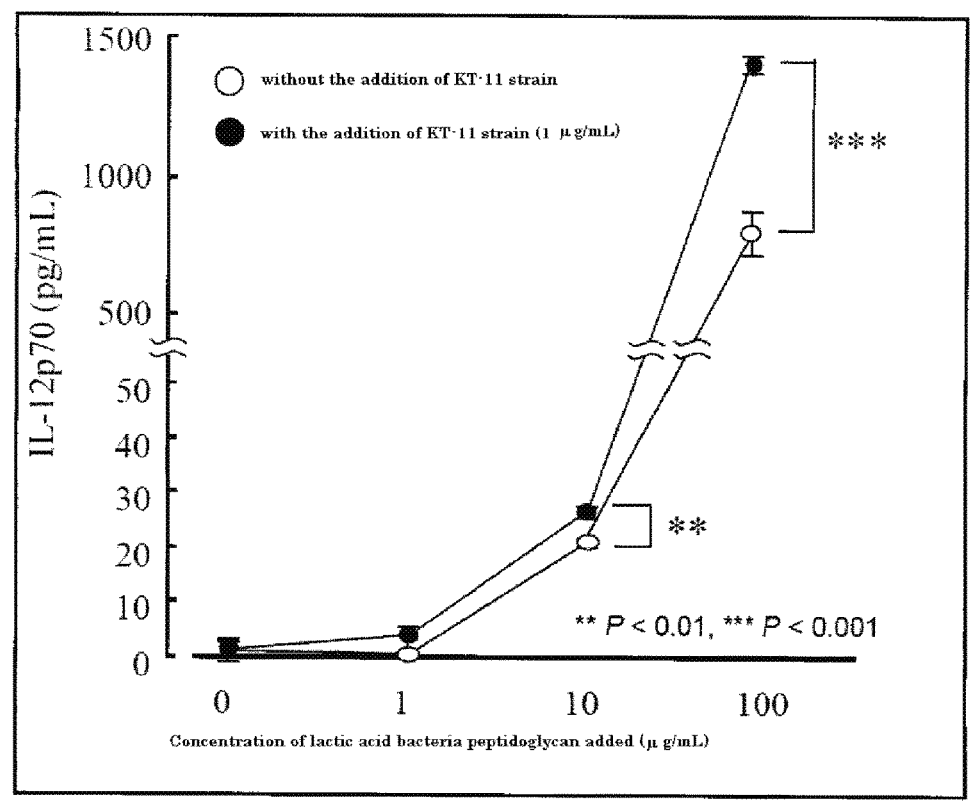

ANTI-ALLERGIC COMPOSITION

TECHNICAL FIELD

The present invention relates to a composition having an anti-allergic action synergistically wherein two or more species of specific lactic acid bacteria are utilized, a method for producing the same, and a pharmaceutical product, food product, supplement, feed, etc. containing the composition.

BACKGROUND ART

T-cells that produce cytokines regulating the growth and function of B-cells, T-cells, etc. and control the immune system are referred to as helper T-cells (Th), which are classified into two types, type 1 helper T-cells (Th1 cells) and type 2 helper T-cells (Th2 cells) based on their cytokine production patterns. Th1 cells are known to produce IFN-γ, IL-2, etc. to activate cellular immunity and Th2 cells to produce IL-4, IL-5, etc. to activate humoral immunity. So-called immune balance generally refers to the balance between the Th1 cells and Th2 cells and is widely used as an index, etc. showing, for example, the allergic condition of a patient.

Allergies are a disease in which various allergic symptoms such as hey fever, rhinitis, and dermatitis are developed when the Th1/Th2 balance is disturbed and shifted abnormally towards the side of Th2 to cause the immune system to respond excessively against a foreign antigen which is harmless in nature. Allergies are classified into 4 types, type I to type IV, depending on the difference in the reaction mechanism. In Japan, the number of patients of type I allergies represented by perennial allergic rhinitis caused by house dust such as ticks and dust and seasonal allergic rhinitis caused by cedar pollens has been significantly increasing, and there is a concern that the number of patients will increase further in the future.

Type I allergies occur with a release of chemical mediators such as histamine by labrocytes upon their stimulation mainly by antigen-bound IgEs. Pollens and house dust came into a body are recognized as antigens to produce IgE antibodies specific to these antigens. The specific IgE antibodies then bind to Fc receptors on the surface of mast cells and basophils in the blood to become sensitized. After that, when the antigen comes into the body again, the antigen binds to the IgE antibody to form an antigen-antibody complex to cause a degranulation, and chemical mediators such as histamine and leukotriene in the granules are released and the actions of these mediators manifest as allergic symptoms.

Examples of drugs used against these allergic symptoms include antihistamines, leukotriene antagonists, thromboxane antagonists, Th2 cytokine inhibitors, mediator-release inhibitors, steroid drugs, etc. However, for example, antihistamines may cause drowsiness and thirst as side effects, while leukotriene antagonists are known to have side effects such as cytopenia and digestive trouble, and mediator-release inhibitors to have side effects such as digestive trouble and bladder inflammation-like symptoms. These drugs therefore are not always safe.

Due to the above background, lactic acid bacteria regulating immune balance and having an anti-allergic action have recently attracted attention as safer anti-allergic materials. For example, the followings have been reported: an IgE antibody production inhibitor comprising as an active ingredient bacterial cells of lactic acid bacteria selected from *Lactobacillus acidophilus, Lactobacillus brevis, Lactobacillus buchneri, Lactobacillus casei, Lactobacillus delbrueckii, Lactobacillus fermentum, Lactobacillus helveticus, Lactobacillus kefir, Lactobacillus paracasei, Lactobacillus plantarum, Lactobacillus rhamnosus, Lactobacillus salivarius, Streptococcus thermophilus, Lactococcus lactis, Lactococcus plantarum, Lactococcus raffinolactis, Leuconostoc lactis, Leuconostoc mesenteroides, Enterococcus faecalis*, and *Enterococcus faecium* (see Patent Document 1); an anti-allergic agent comprising as an active ingredient human-derived bifidobacteria selected from *Bifidobacterium infantis, Bifidobacterium breve, Bifidobacterium longum*, and *Bifidobacterium bifidum* (see Patent Document 2); a type 1 allergy suppressing agent having an histamine release suppressing effect, comprising as an active ingredient bacterial cells of lactic acid bacteria, *Enterococcus faecalis* (AD101 strain) and *Lactobacillus reuteri* (AD0002 strain), separated from the human intestinal bacterial group (see Patent Document 3); and a drink and food product having an anti-allergic function, containing as an active ingredient *Lactobacillus paracasei* (see Patent Document 4).

Further, the followings have been reported: a composition for enhancing immunity containing a mixed culture, or mixed bacterial cells or culture supernatant derived from the mixed culture of three to eight species of lactic acid bacteria and *Saccharomyces cerevisiae*, the lactic acid bacteria being selected from the group consisting of *Lactobacillus delbrueckii, Lactobacillus acidophilus, Lactobacillus plantarum, Lactobacillus fermentum, Lactobacillus casei, Lactobacillus rhamnosus, Lactococcus lactis* and *Streptococcus thermophilus*, (see Patent Document 5); an anti-food allergy agent comprising *Enterococcus faecium* which is lactic acid bacteria stimulating gut immunity or type 1 helper T-cells (see Patent Document 6 and Patent Document 7); an anti-allergic agent comprising as an active ingredient *Bacillus coagulans* which is spore bearing lactic acid bacteria (see Patent Document 8); an anti-allergic agent comprising as an active ingredient viable bacteria, dead bacteria, or a processed product of bacterial cells of at least one lactic acid bacteria selected from lactic acid bacteria belonging to the plant-derived genus *Lactobacillus*, lactic acid bacteria belonging to the plant-derived genus *Leuconostoc*, and lactic acid bacteria belonging to the plant-derived genus *Pediococcus* (see Patent Document 9); fermented milk having an action of inducing the expression of interferon gamma, containing bacterial cells or bacterial-cell components of plural species of lactic acid bacteria selected from the group consisting of *Lactobacillus casei, Lactobacillus plantarum, Lactococcus lactis* subspecies lactis, and *Lactococcus lactis* subspecies cremoris (see Patent Document 10); and an anti-allergic agent comprising a *Lactobacillus plantarum* culture as an active ingredient (see Patent Document 11).

Still further, the followings have been reported: *Pediococcus pentosaceus* which has an immunostimulatory action and/or allergy suppressing action and is resistant to gastric juice (see Patent Document 12); lactic acid bacteria *Streptococcus thermophilus* characterized in having an immunostimulatory action (see Patent Document 13); lactic acid bacteria selected from *Lactobacillus paracasei, Lactobacillus plantarum, Lactobacillus gasseri* and *Lactobacillus salivarius* having an immunostimulatory action/anti-allergic action (see Patent Document 14); *Lactobacillus acidophilus* PM-A0002, *Lactobacillus gasseri, Lactobacillus salivarius, Lactobacillus johnsonii, Lactobacillus acidophilus* PM-A0013 that stimulate immune cells to secrete cytokines at an anti-allergic concentration (see Patent Document 15); an anti-allergic agent containing as an active ingredient lactic acid bacteria belonging to *Leuconostoc mesenteroides* having a high IgE antibody-production suppressing action and an anti-allergic action (see Patent Document 16); an agent for ameliorating pollen allergy symptoms, consisting of *Lactobacillus bulgaricus, Lactobacillus rhamnosus, Lactobacillus acidophilus*, or a cell surface layer or crude peptidoglycans thereof (see Patent Document 17); a composition for regulating immune balance, containing *Lactobacillus paracasei* bacterial cells and *Bifidobacterium bifidum* bacterial cells (see Patent Document 18); *Lactobacillus brevis* which has an immunostimulatory action and/or allergy suppressing action and is resistant to gastric juice (see Patent Document 19); an anti-allergic composition containing *Lactobacillus delbrueckii, Enterococcus durans, Leuconostoc mesenteroides* (see Patent Document 20); and an anti-allergic composition containing *Lactobacillus crispatus* (see Patent Document 21).

PRIOR ART DOCUMENT

Patent Document

Patent Document 1: Japanese Unexamined Patent Application Publication No. 9-2959
Patent Document 2: Japanese Unexamined Patent Application Publication No. 10-309178
Patent Document 3: Japanese Unexamined Patent Application Publication No. 2000-95697
Patent Document 4: Japanese Unexamined Patent Application Publication No. 2005-137357
Patent Document 5: Japanese Unexamined Patent Application Publication No. 2005-68092
Patent Document 6: Japanese Unexamined Patent Application Publication No. 2006-67881
Patent Document 7: Japanese Unexamined Patent Application Publication No. 2006-104107
Patent Document 8: Japanese Unexamined Patent Application Publication No. 2007-55986
Patent Document 9: Japanese Unexamined Patent Application Publication No. 2007-70249
Patent Document 10: Japanese Unexamined Patent Application Publication No. 2007-117031
Patent Document 11: Japanese Unexamined Patent Application Publication No. 2007-126365
Patent Document 12: Japanese Unexamined Patent Application Publication No. 2008-54556
Patent Document 13: Japanese Unexamined Patent Application Publication No. 2008-61512
Patent Document 14: Japanese Unexamined Patent Application Publication No. 2008-99632
Patent Document 15: Japanese Unexamined Patent Application Publication No. 2008-169198
Patent Document 16: Japanese Unexamined Patent Application Publication No. 2008-231094
Patent Document 17: Japanese Unexamined Patent Application Publication No. 2008-255084
Patent Document 18: Japanese Unexamined Patent Application Publication No. 2009-57346
Patent Document 19: Japanese Unexamined Patent Application Publication No. 2009-112232
Patent Document 20: Japanese Unexamined Patent Application Publication No. 2009-142266
Patent Document 21: Japanese Unexamined Patent Application Publication No. 2009-209132

SUMMARY OF THE INVENTION

Object to be Solved by the Invention

An object of the present invention is to provide a composition derived from lactic acid bacteria having an anti-allergic effect (an effect of suppressing allergic symptoms such as hay fever) synergistically, and a food product, pet food, etc. containing the composition.

Means to Solve the Object

In order to suppress allergic symptoms, it is effective to lead the immune balance towards "Th1-type" dominant, and generally, lactic acid bacteria are said to have an activity to lead the immune balance towards "Th1-type" dominant. The present inventors made a keen study to improve the activity of lactic acid bacteria *Lactobacillus crispatus* KT-11 strain (FERM BP-11332), that had been found by the present inventors to have an activity to lead the immune balance towards "Th1-type dominant". As a result, the present inventors found that using at a certain ratio bacterial cells of *Lactobacillus crispatus* KT-11 strain and viable bacteria, dead bacteria, or a processed product of bacterial cells of other lactic acid bacteria belonging to the genus *Lactobacillus*, genus *Bifidobacterium*, genus *Leuconostoc*, genus *Enterococcus*, genus *Pediococcus*, etc. increases synergistically Th1-type cells or the amount of cytokines secreted from Th1-type cells, and thus completed the present invention.

Specifically, the present invention relates to (1) a composition having an anti-allergic action, containing viable bacteria, dead bacteria, or a processed product of bacterial cells of one or more bacterial strains selected from *Lactobacillus crispatus* KT-11 strain (FERM BP-11332), *Lactobacillus crispatus* KT-23 strain (FERM BP-11333), and *Lactobacillus crispatus* KT-25 strain (FERM BP-11334) and viable bacteria, dead bacteria, or a processed product of bacterial cells of other lactic acid bacteria at a biomass-converted ratio of 99:1 to 50:50; (2) the composition according to (1), wherein the biomass-converted ratio is 99:1 to 75:25; (3) the composition according to (1) or (2), wherein other lactic acid bacteria are one or more lactic acid bacteria selected from the group consisting of lactic acid bacteria of the genus *Lactobacillus*, genus *Bifidobacterium*, genus *Leuconostoc*, genus *Enterococcus*, and genus *Pediococcus*; (4) the composition according to (3), wherein the lactic acid bacteria of the genus *Lactobacillus* are one or more lactic acid bacteria selected from the group consisting of *Lactobacillus paracasei, Lactobacillus crispatus, Lactobacillus brevis, Lactobacillus bulgaricus, Lactobacillus rhamnosus*, and *Lactobacillus plantarum*; (5) the composition according to any one of (1) to (4), wherein the dead bacteria are bacterial cells that are heat-treated in a buffer solution; (6) the composition according to any one of (1) to (4), wherein the processed product of bacterial cells is a peptidoglycan derived from lactic acid bacteria; (7) the composition according to any one of (1) to (6), wherein the anti-allergic action is an action of enhancing an interferon gamma (IFN-γ) production ability; and (8) the composition according to any one of (1) to (7), wherein the anti-allergic action is an action of enhancing a IL-12p70 production ability.

The present invention further relates to (9) a pharmaceutical product containing the composition having an anti-allergic action according to any one of (1) to (8); (10) a drink and food product or a supplement containing the composition having an anti-allergic action according to any one of (1) to (8); (11) a pet food or a pet supplement containing the composition having an anti-allergic action according to any one of (1) to (8); (12) a feed containing the composition having an anti-allergic action according to any one of (1) to (8); (13) a method for producing a composition having an anti-allergic action comprising the following steps (a) to (c):

(a) a step of preparing viable bacteria, dead bacteria, or a processed product of bacterial cells of one or more bacterial strains selected from *Lactobacillus crispatus* KT-11 strain (FERM BP-11332), *Lactobacillus crispatus* KT-23 strain (FERM BP-11333), and *Lactobacillus crispatus* KT-25 strain (FERM BP-11334); (b) a step of preparing viable bacteria, dead bacteria, or a processed product of bacterial cells of other lactic acid bacteria; and (c) a step of formulating the viable bacteria, dead bacteria, or the processed product of bacterial cells prepared in step (a) and the viable bacteria, dead bacteria, or the processed product of bacterial cells prepared in step (b) at a biomass-converted ratio of 99:1 to 50:50; and (14) a method for using a composition containing viable bacteria, dead bacteria, or a processed product of bacterial cells of one or more bacterial strains selected from *Lactobacillus crispatus* KT-11 strain (FERM BP-11332), *Lactobacillus crispatus* KT-23 strain (FERM BP-11333), and *Lactobacillus crispatus* KT-25 strain (FERM BP-11334) and viable bacteria, dead bacteria, or a processed product of bacterial cells of other lactic acid bacteria at a biomass-converted ratio of 99:1 to 50:50, in the preparation of an anti-allergic agent.

Effect of the Invention

According to the present invention, a composition derived from lactic acid bacteria and having an anti-allergic effect synergistically and a pharmaceutical product, food product, supplement, pet food, pet supplement, and feed containing the composition can be provided.

BRIEF DESCRIPTION OF DRAWINGS

FIG. 1 This figure shows the test results evaluating the amount of *Lactobacillus crispatus* KT-11 strain added. A synergistic anti-allergic effect was observed even at the ratio of 1% KT-11 strain and 99% *Lactobacillus plantarum*, and the synergistic effect was significantly observed when KT-11 strain was added at 75 to 99%.

FIG. 2 This figure shows the test results verifying the synergistic effect provided by *Lactobacillus crispatus* KT-11 strain and various species of lactic acid bacteria. Comparisons were made for several species of lactic acid bacteria, between the case of adding each species alone and the case of using each species in combination with KT-11 strain, and it has been verified that KT-11 strain synergistically enhances the anti-allergic effect of other lactic acid bacteria (that the number of Th1-type cells is increased synergistically).

FIG. 3 This figure shows the test results verifying the effect of a combined use of *Lactobacillus crispatus* KT-11 strain and a processed product of bacterial cells of lactic acid bacteria (peptidoglycans). It has been verified that a combined use of dead bacterial cells of KT-11 strain and peptidoglycans derived from *Lactobacillus acidophilus* also provides a synergistically enhanced anti-allergic effect.

MODE OF CARRYING OUT THE INVENTION

The composition having an anti-allergic action (the anti-allergic composition) of the present invention is not particularly limited as long as it is a composition containing viable bacteria, dead bacteria, or a processed product of bacterial cells of one or more bacterial strains selected from *Lactobacillus crispatus* KT-11 strain (FERM BP-11332, deposited since Dec. 4, 2007 at International Patent Organism Depositary, National Institute of Advanced Industrial Science and Technology, Tsukuba Central 6, 1-1, Higashi 1-Chome Tsukuba-shi, Ibaraki-ken 305-8566), *Lactobacillus crispatus* KT-23 strain (FERM BP-11333, deposited since Dec. 4, 2007 at International Patent Organism Depositary, National Institute of Advanced Industrial Science and Technology, Tsukuba Central 6, 1-1, Higashi 1-Chome Tsukuba-shi, Ibaraki-ken 305-8566) and *Lactobacillus crispatus* KT-25 strain (FERM BP-11334, deposited since Dec. 4, 2007 at International Patent Organism Depositary, National Institute of Advanced Industrial Science and Technology, Tsukuba Central 6, 1-1, Higashi 1-Chome Tsukuba-shi, Ibaraki-ken 305-8566), and viable bacteria, dead bacteria, or a processed product of bacterial cells of other lactic acid bacteria at a biomass-converted ratio of 99:1 to 50:50.

Further, the method for producing the composition having an anti-allergic action of the present invention is not particularly limited as long as it is a method comprising the following steps (a) to (c): (a) a step of preparing viable bacteria, dead bacteria, or a processed product of bacterial cells of one or more bacterial strains selected from *Lactobacillus crispatus* KT-11 strain (FERM BP-11332), *Lactobacillus crispatus* KT-23 strain (FERM BP-11333), and *Lactobacillus crispatus* KT-25 strain (FERM BP-11334); (b) a step of preparing viable bacteria, dead bacteria, or a processed product of bacterial cells of other lactic acid bacteria; and (c) a step of formulating the viable bacteria, dead bacteria, or the processed product of bacterial cells prepared in step (a) and the viable bacteria, dead bacteria, or the processed product of bacterial cells prepared in step (b) at a biomass-converted ratio of 99:1 to 50:50. Further, the using method of the present invention is not particularly limited as long as it is a method for using a composition containing viable bacteria, dead bacteria, or a processed product of bacterial cells of one or more bacterial strains selected from *Lactobacillus crispatus* KT-11 strain (FERM BP-11332), *Lactobacillus crispatus* KT-23 strain (FERM BP-11333), and *Lactobacillus crispatus* KT-25 strain (FERM BP-11334) and viable bacteria, dead bacteria, or a processed product of bacterial cells of other lactic acid bacteria at a biomass-converted ratio of 99:1 to 50:50, in the preparation of an anti-allergic agent. A composition, however, containing the above ingredients at a biomass-converted ratio of 99:1 to 75:25, and particularly at the ratio of 75:25 is preferred so as to provide a particularly excellent synergistic effect in the anti-allergic action. In this context, the term "biomass-converted" refers to the conversion based on the mass of wet bacterial cells after a centrifugation of the culture solution of the lactic acid bacteria or on the mass of dried bacterial cells obtained by drying the above wet bacterial cells.

Examples of the above anti-allergic action include the action of enhancing an interferon gamma (IFN-γ) production ability, the action of enhancing a IL-12p70 production ability, the action of suppressing an interleukin 4 (IL-4) production ability, the action of suppressing an immunoglobulin E (IgE) production ability, etc., and examples of allergies include allergic diseases such as hey fever, atopic dermatitis, allergic bronchial asthma, allergic rhinitis, food allergy, allergic conjunctivitis, allergic urticaria, etc.

As the above other lactic acid bacteria, lactic acid bacteria belonging to the genus *Lactobacillus*, genus *Bifidobacterium*, genus *Leuconostoc*, genus *Enterococcus*, genus *Pediococcus*, genus *Lactococcus*, genus *Streptococcus*, etc. can be preferably exemplified, and one or more species of these lactic acid bacteria can be used. As the lactic acid bacteria belonging to the above genus *Lactobacillus*, *Lactobacillus paracasei*, *Lactobacillus crispatus* (with the proviso that KT-11 strain, KT-23 strain and KT-25 strain are excluded), *Lactobacillus brevis, Lactobacillus bulgaricus, Lactobacillus rhamnosus, Lactobacillus plantarum, Lactobacillus acidophilus, Lactobacillus casei, Lactobacillus delbrueckii, Lactobacillus fermentum, Lactobacillus salivarius, Lactobacillus johnsonii, Lactobacillus helveticus, Lactobacillus kefir*, etc. can be exemplified. As the lactic acid bacteria belonging to the above genus *Bifidobacterium, Bifidobacterium infantis, Bifidobacterium breve, Bifidobacterium longum, Bifidobacterium bifidum*, etc. can be exemplified. As the lactic acid bacteria belonging to the above genus *Leuconostoc, Leuconostoc lactis, Leuconostoc mesenteroides*, etc. can be exemplified. As the lactic acid bacteria belonging to the above genus *Enterococcus, Enterococcus faecalis, Enterococcus durans, Enterococcus faecium*, etc. can be exemplified. As the lactic acid bacteria belonging to the above genus *Pediococcus, Pediococcus pentosaceus*, etc. can be exemplified. As the lactic acid bacteria belonging to the above genus *Lactococcus, Lactococcus lactis, Lactococcus plantarum, Lactococcus raffinolactis*, etc. can be exemplified. As the lactic acid bacteria belonging to the above genus *Streptococcus, Streptococcus thermophilus*, etc. can be exemplified.

The lactic acid bacteria of the present invention can be used in the form of viable bacteria, dead bacteria, or a processed product of their bacterial cells. As the above viable bacteria, dead bacteria, or a processed product of their bacterial cells, a culture solution of the lactic acid bacteria, wet bacterial cells obtained after a centrifugation of the culture solution of the lactic acid bacteria, a washed product thereof and its lyophilized powder, and heat killed bacterial cells, dried killed bacterial cells, bacterial homogenates such as bacterial cell wall, bacterial lysate thereof etc. can be exemplified. Killed bacterial cells that were heat-treated in a buffer solution, killed bacterial cells obtained by a lyophilization and a subsequent heat-treatment of bacterial cells in a buffer solution, and peptidoglycans from lactic acid bacteria can be more preferably exemplified.

The composition having an anti-allergic action of the present invention can be advantageously used for a pharmaceutical product, drink and food product or supplement, pet food or pet supplement, feed, etc. When using the anti-allergic composition of the present invention as a pharmaceutical product or a supplement for preventing/treating an allergic disease, various ingredients to be combined to prepare drugs, such as a pharmaceutically acceptable common carrier, binder, stabilizer, excipient, diluent, pH buffer, disintegrant, solubilizer, solubilizing agent, isotonic agent, etc. can be added. Further, in addition to these, known anti-allergic agents can be used in combination. These pharmaceutical products such as preventative/therapeutic agents can be administered orally or parenterally. Specifically, the pharmaceutical products can be administered orally in a commonly used dosage form, for example, as powder, granules, capsules, syrup, suspension, etc., or administered parenterally as an injection prepared in the dosage form of a solution, emulsion, suspension, etc., and in addition, can be administered intranasally as a spray, and of these, oral administrations are preferred. The dosage amount can be appropriately selected depending on the purpose of administration, either preventative or therapeutic, the type and severity of the bone disease, age of the patient, etc.

Further, the types of food products and food materials used for preventing/treating allergy, added with the anti-allergic composition of the present invention are not particularly limited, and for example, include the followings: yogurt, various drinks such as yogurt drink, juice, milk, soymilk, alcohols, coffee, tea, green tea, oolong tea, and sports drink; bread and confectionery including baked confectionery such as a pudding, cookie, bread, cake, jelly, rice cracker, Japanese confectionery such as azuki-bean jelly, frozen dessert, chewing gum, etc.; noodles such as wheat noodle and buckwheat noodle; fish jelly products such as boiled fish paste, ham, and fish sausage; seasonings such as bean paste, soy sauce, dressing, mayonnaise, and sweetener; dairy products such as cheese and butter; bean curd and konjaku; and other various prepared foods such as food boiled in soy sauce, dumpling, croquette and salad. A known anti-allergic agent can be used in combination in these food products and food materials.

Further, a feed formulated with the anti-allergic composition of the present invention can be advantageously used for farming, etc. domestic animals and domestic fowls such as pigs, cows and chickens, pets such as dogs and cats, and cultured fish and shellfish. A known anti-allergic agent can be used in combination in the feed.

Hereinbelow, the present invention will be described with reference to Examples. However, the technical scope of the present invention is not limited to the content of the description of Examples.

EXAMPLE 1

(Synergistic Action on Anti-Allergic Effect Based on Difference in Addition Ratio)

It is shown hereinbelow the synergistic action of *Lactobacillus crispatus* KT-11 strain (FERM BP-11332) on anti-allergic effect based on the difference in addition ratio.

(Preparation of Bacterial-Cell Sample Solution)

*Lactobacillus crispatus* KT-11 strain or *Lactobacillus plantarum* JCM $1149^T$ was inoculated on an MRS liquid medium respectively, and cultured at 37° C. for 24 hours. After the culture, the bacterial cells were collected by centrifugation (2,000 rpm, 10 minutes) and washed three times with distilled water. The washed bacterial cells were lyophilized, then suspended and heat-treated (65° C., 30 minutes) in a sterile 0.15 M sodium chloride-0.01 M phosphate buffer solution (PBS, pH 7.2) to provide a bacterial-cell sample solution.

(Preparation and Culture of Peyer's Patch Cell Suspension)

Intestinal Peyer's patch was removed from a 6 week-old male C3H/HeN mouse, and the cells were suspended in a RPMI-1640 medium containing 5% fetal bovine serum (FBS), 100 U/mL Penicillin G sodium, and 100 μg/mL streptomycin sulfate. After washed and centrifuged (4° C., 1,300 rpm, 15 minutes) twice in the above medium, a suspension of the Peyer's patch cells was prepared so that the number of viable cells is $1.0 \times 10^6$/mL.

The Peyer's patch cell suspension prepared above was aliquoted in 1 mL to each well of a 48-well flat-bottom microplate, and a bacterial-cell sample solution that had been prepared by changing the combination ratio of *Lactobacillus crispatus* KT-11 strain and *Lactobacillus plantarum* JCM $1149^T$ so that the final concentration was 10 μg/mL in total was added to the each well in 100 μL, then the resultant mixture was cultured at 37° C. in the presence of 5% $CO_2$ for 48 hours.

(Change in Number of IFN-γ Producing Helper T-Cells)

The cultured Peyer's patch cell suspension was washed by centrifugation (4° C., 12,000 rpm, 3 seconds) in a Hank's Balanced Salt Solution (HBSS) containing 1 m MEDIA and 5% FBS. $1.0 \times 10^6$ of the washed Peyer's patch cells were suspended in 1 mL of an activation medium (a 10% FBS-containing RPMI-1640 medium containing 20 μg/mL brefeldin A, 2 μg/mL ionomycin, and 20 ng/mL phorbol 12-myristate 13-acetate), cultured at 37° C. in the presence of 5% $CO_2$ for 4 hours to produce and accumulate cytokines in the cells.

The cultured Peyer's patch cells were washed by centrifugation in HBSS (4° C., 12,000 rpm, 3 seconds), and then 1 μL of biotin-labeled anti-mouse CD4 antibody was added thereto to react at 4° C. for 15 minutes. 1 μL of Streptavidin-PE/Cy5 was further added and the resultant was left at 4° C. under shade for 15 minutes. The reaction solution was washed with HBSS (4° C., 12,000 rpm, 3 seconds), then 100 μL of IntraPrep Reagent 1 was added thereto and the resultant was left at room temperature under shade for 15 minutes to immobilize the cells. This was followed by a wash with HBSS (4° C., 12,000 rpm, 3 seconds), then 100 μL of IntraPrep Reagent 2 was added to react at room temperature under shade for 15 minutes for membrane permeabilization. Next, to measure IFN-γ which is one of Th1 cytokines, 1 μL of phycoerythrin (PE)-labeled anti-mouse IFN-γ antibody was added, left at room temperature under shade for 15 minutes, and then washed by centrifugation in HBSS again (4° C., 12,000 rpm, 3 seconds). After the wash, the number of IFN-γ producing helper T-cells (the number of IFN-γ$^+$CD4$^+$ cells) in the Peyer's patch cells was measured using Guava Personal Cell Function Analyzer (Guava PCA).

FIG. 1 shows the number of IFN-γ producing helper T-cells in the Peyer's patch cells in relative values when *Lactobacillus crispatus* KT-11 strain and *Lactobacillus plantarum* JCM 1149$^T$ were added at each percentage. The relative values are based on the number of IFN-γ producing helper T-cells as 100% when the ratio of *Lactobacillus crispatus* KT-11 strain:*Lactobacillus plantarum* JCM 1149$^T$ is 0:100. The relative value of the number of IFN-γ producing helper T-cells significantly increased when the ratio of *Lactobacillus crispatus* KT-11 strain:*Lactobacillus plantarum* JCM 1149$^T$ was 99:1, 90:10, and 75:25 as compared to a case when the ratio was 0:100 or 100:0. From the above, it is possible to consider that the synergistic effect of *Lactobacillus crispatus* KT-11 strain on anti-allergic effect can be obtained when *Lactobacillus crispatus* KT-11 strain and *Lactobacillus plantarum* JCM 1149$^T$ are added at a ratio of 99:1 to 50:50, particularly at a ratio of 99:1 to 75:25.

EXAMPLE 2

(Advantage of Synergistic Action on Anti-Allergic Effect)

The synergistic action of *Lactobacillus crispatus* KT-11 strain on anti-allergic effect is shown below.

(Preparation of Bacterial-Cell Sample Solution)

Test bacteria shown in Table 1 were prepared respectively in the same manner as in Example 1, and *Lactobacillus crispatus* KT-11 strain and each strain of the test bacteria were mixed at the ratio of 75:25 to provide bacterial-cell sample solutions.

TABLE 1

List of test bacteria

*Bifidobacterium bifidum* NBRC14252$^T$
*Lactobacillus paracasei* NBRC15889$^T$
*Lactobacillus bulgaricus* JCM1002$^T$
*Lactobacillus plantarum* JCM1149$^T$
*Lactobacillus crispatus* JCM1185$^T$
*Lactobacillus rhamnosus* ATCC53103

TABLE 1-continued

List of test bacteria

*Leuconostoc mesenteroides* (Sceti)
*Lactobacillus brevis* (Sceti)

(Preparation and Culture of Peyer's Patch Cell Suspension and Change in the Number of IFN-γ Producing Helper T-Cells)

A Peyer's patch cell solution was prepared and cultured in the same manner as in Example 1. Subsequently, the Peyer's patch cell suspension was aliquoted in 1 mL to each well of a 48-well flat-bottom microplate, and a bacterial-cell sample solution prepared at each concentration was added in 100 μL to the each well, then the resultant mixture was cultured at 37° C. in the presence of 5% $CO_2$ for 48 hours. Change in the number of IFN-γ producing helper T-cells was measured in the same manner as in Example 1.

FIG. 2 shows the number of IFN-γ producing helper T-cells in the Peyer's patch cells as relative values when *Lactobacillus crispatus* KT-11 strain and each strain of test bacteria were added. The values are based on the number of IFN-γ producing helper T-cells as 100% when 7.5 μg/mL *Lactobacillus crispatus* KT-11 strain alone was added. The relative value of the number IFN-γ producing helper T-cells was significantly high when both *Lactobacillus crispatus* KT-11 strain and test bacteria were added as compared to when *Lactobacillus crispatus* KT-11 strain alone or a test bacterial strain alone was added. This demonstrates that *Lactobacillus crispatus* KT-11 strain has a higher anti-allergic affect than conventional lactic acid bacteria.

EXAMPLE 3

(Preparation of Bacterial-Cell Sample Solution)

Test bacteria shown in Table 1 were prepared respectively in the same manner as in Example 1 to provide bacterial-cell sample solutions.

(Culture of Mouse Macrophage-Like Cell Line)

J774.1 cells, a mouse macrophage-like cell line, were used after suspended in a RPMI-1640 medium containing 5% FBS, 100 U/mL Penicillin G sodium and 100 μg/mL streptomycin sulfate, and cultured to confluence in a sterile plastic petri dish at 37° C. under 5% $CO_2$. J774.1 cell suspension prepared at 1×10$^6$/mL was aliquoted in 1 mL to a 48-well flat-bottom microplate, and 100 μL each of a bacterial-cell sample solution of *Lactobacillus crispatus* KT-11 strain prepared so that the final concentration was 0 or 1 μg/mL and a commercially available *Lactobacillus acidophilus*-derived peptidoglycan solution (Peptidoglycan type II, Wako Pure Chemical Industries, Ltd.) dissolved in PBS were added respectively to each well and cultured at 37° C. in the presence of 5% $CO_2$ for 48 hours, followed by a centrifugation at 4° C., 2000 rpm for 15 minutes, and the culture supernatant fluid was collected.

(Production of IL-12p70)

The amount of IL-12p70 in the culture supernatant fluid was measured employing an enzyme immunoassay (ELISA). Specifically, 100 μL of 0.1 M carbonate buffer solution (pH 9.6) containing 100 μg/mL anti-mouse IL-12p70 antibody and 4% bovine serum albumin (BSA) was aliquoted to each well of a 96-well microplate and allowed to stand at 4° C. overnight. After a wash with PBS containing 0.05% Tween 20 (PBS-T), 300 μL of 0.1 M carbonate buffer solution containing 0.4% BSA was added, and the resultant mixture was allowed to stand at 25° C. for 120 minutes. After a wash with PBS-T again, the culture supernatant fluid diluted at the optimum ratio with PBS-T containing 0.4% BSA and 2% polyvinylpyrrolidone (PVP) was aliquoted in 100 μL to the each well to react at 25° C. for 120 minutes. Further, after a wash with PBS-T, a biotin-labeled anti-mouse IL-12p70 antibody solution diluted at the optimum ratio with PBS-T containing 2% PVP was aliquoted in 100 μL to the each well to react at 25° C. for 60 minutes. Subsequently, after a wash with PBS-T, a horseradish peroxidase (HRP)-labeled streptavidin solution diluted at the optimum ratio with PBS-T containing 2% PVP was aliquoted in 100 μL to the each well to react at 25° C. for 30 minutes. A TMB solution was aliquoted in 100 μL to the each well to react under a complete shade at 25° C. for 30 minutes, and then 4N sulfuric acid was aliquoted in 100 μL to the each well to stop the reaction, followed by an immediate measurement of absorbance at 450 nm using Bio-Rad model 550 microplate reader. The amount of IL-12p70 was calculated by a standard curve obtained from IL-12p70 at a known concentration.

FIG. 3 shows the amount of IL-12p70 which is a Th1 cytokine, in the culture solution supernatant of J774.1 cells cultured with the addition of a commercially available lactic acid peptidoglycan. The significance of the results of adding *Lactobacillus crispatus* KT-11 strain was determined by Student's t-test, based on the amount of IL-12p70 without the addition of *Lactobacillus crispatus* KT-11 strain as the standard. The amount of IL-12p70 in the culture solution supernatant of J774.1 cells cultured with the addition of 10 μg/mL and 100 μg/mL commercially available lactic acid peptidoglycans significantly increased when *Lactobacillus crispatus* KT-11 strain was added as compared to the case without the addition of *Lactobacillus crispatus* KT-11 strain.

This demonstrates that *Lactobacillus crispatus* KT-11 strain synergistically enhances the anti-allergic action of peptidoglycans that are a main cell-wall component of lactic acid bacteria.

The invention claimed is:

1. A method for producing a composition comprising the following steps (a) to (d):
   (a) a step of preparing viable bacteria, dead bacteria, or a processed product comprising all of the components of a bacteria cell, wherein the bacteria is *Lactobacillus crispatus* KT-11 strain (FERM BP-11332);
   (b) a step of preparing viable bacteria, dead bacteria, or a processed product comprising all of the components of a bacteria cell, wherein the bacteria is selected from the group consisting of *Bifidobacterium bifidum* NBRC14252, *Lactobacillus paracasei* NBRC15889, *Lactobacillus bulgaricus* JCM1002, *Lactobacillus plantarum* JCM1149, *Lactobacillus crispatus* JCM1185, *Lactobacillus rhamnosus* ATCC53103, *Leuconostoc mesenteroides*, and *Lactobacillus brevis*;
   (c) a step of formulating said viable bacteria, said dead bacteria, or said processed product prepared in step (a) and said viable bacteria, said dead bacteria, or said processed product prepared in step (b) at a biomass-converted ratio of 99:1 to 50:50; and
   (d) a step of preparing a composition for oral administration having an action of synergistically enhancing an interferon gamma (IFN-gamma) production ability by adding an effective amount of a formulation formulated in step (c), for administering the composition to an allergic disease patient.

\* \* \* \* \*